US009812309B2

(12) United States Patent
Hoyes et al.

(10) Patent No.: US 9,812,309 B2
(45) Date of Patent: Nov. 7, 2017

(54) MICROWAVE CAVITY RESONATOR DETECTOR

(71) Applicant: Micromass UK Limited, Wilmslow (GB)

(72) Inventors: John Brian Hoyes, Stockport (GB); Keith Richardson, Derbyshire (GB)

(73) Assignee: Micromass UK Limited, Wilmslow (GB)

( * ) Notice: Subject to any disclaimer, the term of this patent is extended or adjusted under 35 U.S.C. 154(b) by 0 days.

(21) Appl. No.: 15/101,688

(22) PCT Filed: Dec. 5, 2014

(86) PCT No.: PCT/GB2014/053627
§ 371 (c)(1),
(2) Date: Jun. 3, 2016

(87) PCT Pub. No.: WO2015/082939
PCT Pub. Date: Jun. 11, 2015

(65) Prior Publication Data
US 2017/0018414 A1    Jan. 19, 2017

(30) Foreign Application Priority Data

Dec. 5, 2013   (GB) .................................. 1321524.9
Apr. 4, 2014   (EP) .................................. 14163504
Apr. 24, 2014  (GB) .................................. 1407235.9

(51) Int. Cl.
  H01J 49/00   (2006.01)
  H01J 43/02   (2006.01)
  (Continued)

(52) U.S. Cl.
  CPC ............ H01J 49/025 (2013.01); G01N 30/72 (2013.01); G01T 1/20 (2013.01); H01J 40/00 (2013.01);
  (Continued)

(58) Field of Classification Search
  CPC ...... H01J 49/025; H01J 49/00; H01J 49/0031; H01J 49/401; H01J 43/00; H01J 43/02;
  (Continued)

(56) References Cited

U.S. PATENT DOCUMENTS 6,080,985 A    6/2000  Welkie et al.
7,038,197 B2   5/2006  Bateman et al.
(Continued)

FOREIGN PATENT DOCUMENTS

GB    2388704    11/2003
JP    60130031   7/1985
(Continued)

OTHER PUBLICATIONS

Watson, J. T. et al., Introduction to mass spectrometry: instrumentation, applications, and strategies for data interpretation, pp. 53-172, Jan. 2007.

*Primary Examiner* — Wyatt Stoffa
*Assistant Examiner* — Hanway Chang
(74) *Attorney, Agent, or Firm* — Diederiks & Whitelaw, PLC

(57) ABSTRACT

An ion detector system for a mass spectrometer is disclosed comprising a first device arranged and adapted to receive ions and emit or output first electrons and a microwave cavity resonator arranged and adapted to deflect the first electrons onto a first detector.

20 Claims, 14 Drawing Sheets

(51) Int. Cl.
  *G01N 30/00* (2006.01)
  *G01T 1/16* (2006.01)
  *H01J 49/02* (2006.01)
  *G01T 1/20* (2006.01)
  *G01N 30/72* (2006.01)
  *H01J 40/00* (2006.01)
  *H01J 49/40* (2006.01)

(52) U.S. Cl.
  CPC .......... *H01J 43/02* (2013.01); *H01J 49/0031* (2013.01); *H01J 49/401* (2013.01)

(58) Field of Classification Search
  CPC ........ G01N 30/00; G01N 30/62; G01N 30/72; G01T 1/16; G01T 1/20
  USPC .................................................. 250/281, 282
  See application file for complete search history.

(56) References Cited

U.S. PATENT DOCUMENTS

| | | |
|---|---|---|
| 7,446,296 B2 | 11/2008 | Kinoshita |
| 7,858,937 B2 | 12/2010 | Ogawa et al. |
| 8,669,521 B2 | 3/2014 | Blick et al. |
| 8,829,427 B2 | 9/2014 | Brouard et al. |
| 2009/0272890 A1 | 11/2009 | Ogawa et al. |
| 2010/0123073 A1 | 5/2010 | Guest et al. |
| 2012/0074313 A1 | 3/2012 | Blick et al. |

FOREIGN PATENT DOCUMENTS

| | | |
|---|---|---|
| JP | 05174783 | 7/1993 |
| WO | 2012010894 | 1/2012 |

Typical potential diagram (floated flight tube in positive ion mode)

Typical potential diagram (floated flight tube in negative ion mode)

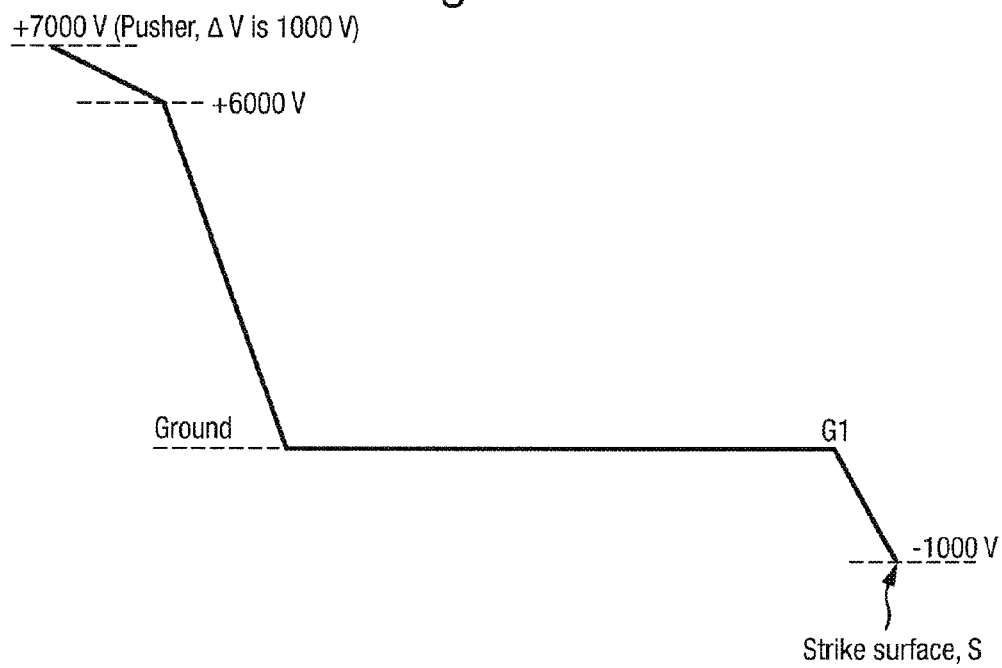
Typical potential diagram (grounded flight tube in positive ion mode)
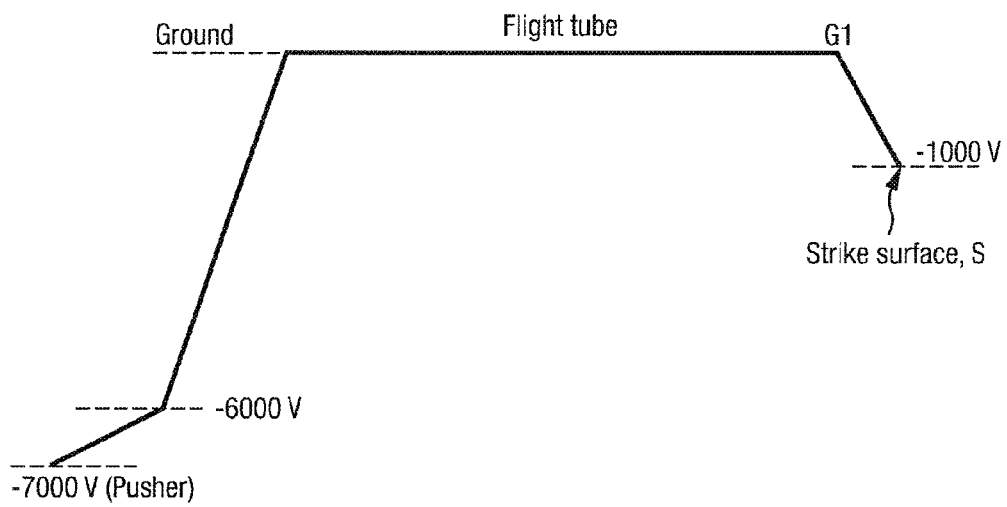
Typical potential diagram (grounded flight tube in negative ion mode)

Typical potential diagram for cavity resonator, MCP and PDA

MICROWAVE CAVITY RESONATOR DETECTOR

CROSS REFERENCE TO RELATED APPLICATION APPLICATIONS

This application is the National Stage of International Application No. PCT/GB2014/053627, filed 5 Dec. 2014 which claims priority from and the benefit of United Kingdom patent application No. 1321524.9 filed on 5 Dec. 2013, European patent application No. 14163504.5 filed on 4 Apr. 2014 and United Kingdom patent application No. 1407235.9 filed on 24 Apr. 2014. The entire contents of these applications are incorporated herein by reference.

BACKGROUND TO THE PRESENT INVENTION

The present invention relates to an ion detector system for a mass spectrometer, a mass spectrometer, a method of detecting ions, a method of mass spectrometry, a time of flight mass analyser, a method of operating a time of flight mass analyser, a photon detection system, a streak camera detector and a method of detecting photons. The preferred embodiment relates to an ion detector system for a Time of Flight mass spectrometer.

Streak cameras are known and are versatile detection instruments for detecting light in a manner which gives temporal information. It is known, for example, to use a streak camera to measure electron bunches in synchrotrons and also to measure ultra fast (i.e. femtosecond) laser pulses. It is also known to use streak cameras in plasma physics experiments.

Conventional streak cameras convert pulsed incident light to electrons using a photocathode. The electrons which are emitted from the photocathode are then accelerated by a mesh electrode. The electrons are then arranged to pass between two parallel plate electrodes. A temporally varying sweep voltage is applied to the plate electrodes such that the electrons receive a deflection. The electrons are then arranged to impinge upon a phosphorescent screen.

The signal from the phosphorescent screen is read by a position sensitive detector ("PSD"). The position of the signal on the screen is directly related to the instantaneous sweep voltage that the electrons encountered when the electrons passed rapidly between the two deflection plates whilst a sweep voltage was being applied to the deflection plates.

It will be apparent that streak cameras operate by converting temporal information into spatial information. As a result, depending upon the application, this process reduces the requirements placed upon high speed digitising electronics which are used to capture the signal and/or increases the overall temporal resolution of the detector.

The streak camera principle has been applied to the detection of heavy ions in the radioactive ion beam research facility at RIKEN (Japan). Two streak cameras were used to register secondary electrons produced by a heavy highly energetic ion passing through thin metallic films. The device employed 100 MHz waveforms to deflect an ion beam in x- and y-dimensions onto a phosphor screen. The phosphorescence was then amplified and captured by a Charged Coupled Device ("CCD") camera.

WO 2012/010894 (ISIS) discloses a charged particle spectrum analysis apparatus. FIG. 1 of WO 2012/010894 shows an arrangement wherein sample ions 5 impinge upon a first set of microchannel plates 3 converting the ions into an amplified beam of electrons 7. The beam of electrons 7 is collimated by a slit 9 placed behind the microchannel plates 3. Electrons 7 emitted from the microchannel plates 3 are accelerated through the slit 9 and are subjected to a ramped deflection pulse by two parallel deflection plates 11. The electrons 7 are deflected onto a position sensitive detector 15. The ramp voltage is synchronised to the frame rate of a CMOS sensor which is set at 20 MHz (corresponding with a bin width 50 ns).

As digital electronics gets faster so the digitisation frequency of Time to Digital Converters and Analogue to Digital Converters is also predicted to increase. As a result, the deflection plates of conventional streak cameras would need to be swept at increasingly faster rates.

However, as will be understood by those skilled in the art, it is non-trivial to increase the frequency of the deflection voltage waveforms. Furthermore, it will be appreciated that producing an intense electric field for sweeping electrons in a streak camera in synchronisation with current state of the art digitisers capable of running at bin widths of e.g. 100 ps or faster is technically extremely challenging and the cost would render any such detector system commercially unviable.

Accordingly, it is highly problematic to design a low power, cost effective and stable means of deflecting electrons using deflection electrodes in combination with a position sensitive array detector which is capable of operating at the very high speeds which are required by state of the art detector systems for mass spectrometers.

It is therefore desired to provide an improved ion detector system and an improved method of detecting ions.

SUMMARY OF THE PRESENT INVENTION

According to an aspect of the present invention there is provided an ion detector system for a mass spectrometer comprising:

a first device arranged and adapted to receive ions and emit or output first electrons; and a microwave cavity resonator arranged and adapted to deflect the first electrons onto a first detector.

WO 2012/010894 (ISIS) does not teach or suggest using a microwave cavity resonator to deflect a beam of electrons.

In contrast to the arrangement disclosed in WO 2012/010894 (ISIS) which is able to operates on a time scale corresponding to a time bin width of 50 ns, the present invention is able to operate on a time scale corresponding to a sub-bin time width of just 10 ps. It will be apparent therefore that the present invention represents a substantial improvement over the arrangement disclosed in WO 2012/010894 (ISIS).

The first device preferably comprises a conversion dynode. This is in contrast to the arrangement disclosed in WO 2012/010894 (ISIS) which utilises a microchannel plate or photocathode.

The first electrons preferably comprise secondary electrons.

The ion detector system preferably further comprises one or more grid electrodes arranged upstream of the first device wherein the one or more grid electrodes are arranged and adapted to accelerate the ions onto or into the first device.

The ion detector system preferably further comprises a second device arranged and adapted to apply a magnetic field so as to deflect the first electrons towards the microwave cavity resonator.

The first detector preferably comprises one or more microchannel plates.

The first detector is preferably arranged downstream of the microwave cavity resonator.

The first detector is preferably arranged and adapted to receive the first electrons and emit or output second electrons.

The ion detector system preferably further comprises a first position sensitive detector ("PSD").

The first position sensitive detector is preferably arranged downstream of the first detector.

The first position sensitive detector is preferably arranged and adapted to detect the position or location that the second electrons impinge upon the first position sensitive detector.

The first position sensitive detector preferably comprises one or more photo-diode arrays.

The microwave cavity resonator is preferably arranged and adapted to generate electromagnetic waves within the microwave cavity resonator.

The microwave cavity resonator is preferably arranged and adapted to cause the electromagnetic waves to form standing waves within the microwave cavity resonator.

In a mode of operation the standing waves preferably comprise transverse electric or transverse magnetic mode standing waves.

In a mode of operation the standing waves preferably comprise TE101 mode standing waves.

In a mode of operation the standing waves are preferably arranged so as to sinusoidally modulate the first electrons as the first electrons pass through the microwave cavity resonator.

The ion detector system is preferably arranged and adapted to reject signals relating to second electrons impinging upon one or more portions or one or more end portions of the first position sensitive detector.

The microwave cavity resonator is preferably arranged and adapted to accelerate the first electrons as the first electrons pass through the microwave cavity resonator.

The electromagnetic waves preferably have a frequency in a range selected from the group consisting of: (i) 0.3-10 GHz; (ii) 10-20 GHz; (iii) 20-30 GHz; (iv) 30-40 GHz; (v) 40-50 GHz; (vi) 50-60 GHz; (vii) 60-70 GHz; (viii) 70-80 GHz; (ix) 80-90 GHz; (x) 90-100 GHz; (xi) 100-110 GHz; (xii) 110-120 GHz; (xiii) 120-130 GHz; (xiv) 130-140 GHz; (xv) 140-150 GHz; (xvi) 150-160 GHz; (xvii) 160-170 GHz; (xviii) 170-180 GHz; (xix) 180-190 GHz; (xx) 90-100 GHz; (xxi) 200-210 GHz; (xxii) 210-220 GHz; (xxiii) 220-230 GHz; (xxiv) 230-240 GHz; (xxv) 240-250 GHz; (xxvi) 250-160 GHz; (xxvii) 260-270 GHz; (xxviii) 270-280 GHz; (xxix) 280-290 GHz; and (xxx) 290-300 GHz.

According to another aspect of the present invention there is provided a mass spectrometer comprising an ion detector system as described above.

The mass spectrometer preferably further comprises a Time of Flight mass analyser.

The Time of Flight mass analyser preferably further comprises:
a time of flight region; and
one or more orthogonal acceleration electrodes for orthogonally accelerating ions into the time of flight region.

The mass spectrometer preferably further comprises a device arranged and adapted to apply a voltage pulse to the one or more orthogonal acceleration electrodes in order to cause ions to be orthogonally accelerated into the time of flight region.

The mass spectrometer preferably further comprises a device arranged and adapted to generate a beam of third electrons.

The device for generating the beam of third electrons is preferably arranged and adapted to generate the beam of third electrons at substantially the same time that the voltage pulse is applied to the one or more orthogonal acceleration electrodes and/or that ions are orthogonally accelerated into the time of flight region.

The third electrons are preferably passed, in use, through the microwave cavity resonator.

The third electrons are preferably passed, in use, through the microwave cavity resonator in a different direction to the direction of transmission of the first electrons through the microwave cavity resonator.

The mass spectrometer preferably further comprises a third detector for detecting the third electrons.

The third detector preferably comprises one or more microchannel plates.

The third detector is preferably arranged downstream of the microwave cavity resonator.

The third detector is preferably arranged and adapted to receive the third electrons and emit or output fourth electrons.

The mass spectrometer preferably further comprises a second position sensitive detector ("PSD").

The second position sensitive detector is preferably arranged downstream of the third detector.

The second position sensitive detector is preferably arranged and adapted to detect the position or location that the fourth electrons impinge upon the second position sensitive detector.

The mass spectrometer preferably further comprises a control system wherein the control system is arranged and adapted to determine from the detected position or location that the fourth electrons impinge upon the second position sensitive detector a measure of the rising edge of a voltage pulse applied to the one or more orthogonal acceleration electrodes.

The second position sensitive detector preferably comprises one or more photo-diode arrays.

The mass spectrometer preferably further comprises a master clock wherein clock cycles of the master clock are derived from a signal applied to the microwave cavity resonator.

The master clock is preferably arranged so as to be phase locked to the signal applied to the microwave cavity resonator.

According to another aspect of the present invention there is provided a method of detecting ions comprising:
receiving ions on a first device and emitting or outputting first electrons; and
deflecting the first electrons onto a first detector using a microwave cavity resonator.

According to another aspect of the present invention there is provided a method of mass spectrometry comprising a method of detecting ions as described above.

According to an aspect of the present invention there is provided a streak camera detector wherein electron deflection is caused by the action of electromagnetic fields inside a microwave cavity resonator.

According to a further aspect of the present invention there is provided a time of flight mass analyser comprising a time of flight region, one or more orthogonal acceleration electrodes for orthogonally accelerating ions into the time of flight region, a first device configured to apply a voltage pulse to one or more orthogonal acceleration electrodes to orthogonally accelerate ions into the time of flight region, and a second device arranged and adapted to generate a beam of first electrons based on a timing of the voltage pulse applied to the one or more orthogonal acceleration electrodes and/or on a timing that ions are orthogonally accelerated into the time of flight region.

A time of flight mass analyser according to the present invention differs from a conventional time of flight mass analyser by further comprising a second device for generating a beam of electrons, where the generation of the beam of electrons is based on the timing of the application of the voltage pulse to the orthogonal acceleration electrodes.

The time of flight mass analyser preferably further comprises a microwave cavity resonator arranged and adapted to deflect the first electrons onto a detector. In use, the beam of first electrons is preferably passed through the microwave cavity resonator.

The time of flight mass analyser preferably further comprises a device arranged downstream of the time of flight region and which is arranged and adapted to receive the ions and emit or output second electrons. In use, the second electrons are preferably passed through the microwave cavity resonator in a direction orthogonal to the direction of transmission of the first electrons through the microwave cavity resonator.

The time of flight mass analyser preferably further comprises a detector arranged downstream of the microwave cavity resonator, wherein the detector is arranged and adapted to detect the beam of first electrons. Thus, the detector is preferably arranged to detect the beam of first electrons after the beam of electrons has passed through the microwave cavity resonator.

The detector preferably comprises one or more microchannel plates adapted and arranged to receive the beam of first electrons and emit secondary electrons.

The time of flight mass analyser preferably further comprises a position sensitive detector arranged downstream of the one or more microchannel plates, and the position sensitive detector is arranged and adapted to detect the position or location at which the secondary electrons impinge upon the detector.

By detecting the position or location at which the secondary electrons impinge upon the detector it is possible to determine the time at which the beam of first electrons arrive at the microwave cavity resonator, which in turn provides a measure of the start timing of the beam of first electrons. Since the beam of first electron is generated based on the timing of the voltage pulse applied to the one or more orthogonal acceleration electrodes that orthogonally accelerate the ions, the start timing of the beam of first electrons thus provides a measure of the initiation of the acceleration pulse.

The time of flight mass analyser preferably further comprises a control system arranged and adapted to determine, from the detected position or location that the secondary electrons impinge upon the position sensitive detector, a measure of the rising edge of the voltage pulse applied to the one or more orthogonal acceleration electrodes.

The second device is preferably arranged and adapted to generate the beam of first electrons by applying a pulse that is derived from or dependent upon the voltage pulse applied to the one or more orthogonal acceleration electrodes. Thus, the pulse of first electrons is generated at substantially the same time as the ions are orthogonally accelerated into the time of flight region.

According to another aspect of the present invention there is provided a mass spectrometer comprising a time of flight mass analyser as described above.

Yet another aspect of the present invention provides a method of operating a time of flight mass analyser comprising applying a voltage pulse to one or more orthogonal acceleration electrodes to orthogonally accelerate ions into a time of flight region, and generating a beam of first electrons based on a timing of a voltage pulse applied to one or more orthogonal acceleration electrodes and/or on a timing that ions are orthogonally accelerated into the time of flight region.

According to another further aspect of the present invention there is provided a photon detection system comprising a first device arranged and adapted to receive photons and emit or output first electrons, and a microwave cavity resonator arranged and adapted to deflect the first electrons onto a first detector.

The use of a microwave cavity resonator to deflect a beam of electrons is in contrast to conventional arrangements, such as is disclosed in WO 2012/010894 (ISIS), which use parallel deflection plates. Compared to conventional arrangements which are able to operate on a time scale corresponding to a time bin width of 50 ns, the present invention is able to operate on a time scale corresponding to a sub-bin time width of just 10 ps. It will be apparent therefore that the present invention represents a substantial improvement over the conventional arrangements.

The photon detection system preferably comprises a first detector. The first detector is preferably arranged downstream of the microwave cavity resonator and is preferably arranged and adapted to receive the first electrons and emit or output second electrons.

The photon detection system preferably further comprises a position sensitive detector arranged downstream of the first detector and which is arranged and adapted to detect the position or location at which the second electrons impinge upon the position sensitive detector.

The photon detection system preferably further comprises a second device arranged and adapted to apply a magnetic field so as to deflect the first electrons towards the microwave cavity resonator.

The microwave cavity resonator is preferably arranged and adapted to generate electromagnetic standing waves within the microwave cavity resonator.

In a mode of operation the standing waves preferably comprise transverse electric or transverse magnetic mode standing waves.

In a mode of operation the standing waves preferably comprise TE101 mode standing waves.

The microwave cavity resonator is preferably arranged and adapted such that, in a mode of operation, the first electrons are sinusoidally modulated by the electromagnetic standing waves as the first electrons pass through the microwave cavity resonator.

The microwave cavity resonator is preferably arranged and adapted to accelerate the first electrons as the first electrons pass through the microwave cavity resonator.

The microwave cavity resonator is preferably arranged and adapted to accelerate the first electrons as the first electrons pass through the microwave cavity resonator.

The electromagnetic waves preferably have a frequency in a range selected from the group consisting of: (i) 0.3-10 GHz; (ii) 10-20 GHz; (iii) 20-30 GHz; (iv) 30-40 GHz; (v) 40-50 GHz; (vi) 50-60 GHz; (vii) 60-70 GHz; (viii) 70-80 GHz; (ix) 80-90 GHz; (x) 90-100 GHz; (xi) 100-110 GHz; (xii) 110-120 GHz; (xiii) 120-130 GHz; (xiv) 130-140 GHz; (xv) 140-150 GHz; (xvi) 150-160 GHz; (xvii) 160-170 GHz; (xviii) 170-180 GHz; (xix) 180-190 GHz; (xx) 90-100 GHz; (xxi) 200-210 GHz; (xxii) 210-220 GHz; (xxiii) 220-230 GHz; (xxiv) 230-240 GHz; (xxv) 240-250 GHz; (xxvi)

250-160 GHz; (xxvii) 260-270 GHz; (xxviii) 270-280 GHz; (xxix) 280-290 GHz; and (xxx) 290-300 GHz.

The system may preferably further comprise a master clock configured to derive clock cycles from a signal applied to the microwave cavity resonator.

The master clock may preferably be configured to be phase locked to the signal applied to the microwave cavity resonator.

According to another aspect of the present invention, there is provided a streak camera detector comprising a photon detection system as described above.

Compared to a conventional streak camera detector, a streak camera detector according to the present invention differs by using a microwave cavity resonator instead of parallel plate electrodes to deflect electrons.

According to another aspect of the present invention there is provided a method of detecting photons comprising receiving photons on a first device and emitting or outputting first electrons, and deflecting the first electrons onto a first detector using a microwave cavity resonator.

The preferred embodiment of the present invention relates to an improvement to existing apparatus, specifically multiple pixel or position sensitive Time of Flight mass spectrometer detectors.

According to a preferred embodiment of the present invention ions which have been temporally separated by a Time of Flight mass analyser are arranged to strike a conversion dynode. Secondary electrons are released from the conversion dynode and the secondary electrons are preferably accelerated through a microwave cavity resonator ("MCR") onto a microchannel plate ("MCP") detector. The microchannel plate detector is preferably followed by a position sensitive detector ("PSD") which is capable of continuous high frequency operation. The position sensitive detector preferably comprises a photodiode array ("PDA").

The secondary electrons are preferably deflected by the microwave cavity resonator such that the electrons strike different positions on the position sensitive detector according to the phase of the fields inside the cavity resonator. The frequency of the oscillating field inside the microwave cavity resonator is preferably phase locked to the main clock frequency (bin width) of the read out of the position sensitive detector. The oscillating field periodic time is preferably 4× the bin width of the main position sensitive detector.

The preferred embodiment preferably allows a significant improvement in the speed of the acquisition system enabling the time of flight of ions to be determined to a sub-time bin width of 10 ps.

The bin width is the width in time of the digitisation of a Time to Digital Converter or Analogue to Digital Converter used in the position sensitive detector. It is the reciprocal of the digitisation frequency in Time to Digital Converters or Analogue to Digital Converters, or the frame rate of a streak camera.

The present invention addresses the problem of faster ion detection speeds.

The detection system disclosed in WO 2012/010894 (ISIS) is much slower in comparison to the detection system according to the present invention.

In other embodiments of the present invention, in a Time of Flight mass analyser, a pulse of electrons is preferably produced using passive components. The pulse of electrons is preferably generated at substantially the same time as the main acceleration pulse that is applied to one or more orthogonal acceleration electrodes in order to accelerate ions into the time of flight region. Measuring the timing of the pulse of electrons provides a measure of the start timing or rising edge of the main acceleration voltage pulse.

Since the pulse of electrons is preferably produced using passive components, there is advantageously no inherent jitter. The preferred embodiment therefore allows the start timing or rising edge of the main acceleration voltage pulse to be determined more accurately, potentially to a precision of better than 10 ps, thereby addressing the problem of start timing precision.

Further embodiments of the present invention relate to an improvement to streak camera detectors. A streak camera detector according to embodiments of the present invention differs from conventional streak camera detector in that a microwave cavity resonator is used instead of parallel deflection plate for deflecting electrons. The microwave cavity resonator is preferably configured to generate electromagnetic waves that form standing waves within the microwave cavity resonator thereby allowing a high frequency time-varying deflection field to be generated and maintained, thus addressing the problem of higher frequency and more stable deflection field.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; and (xxvi) a Solvent Assisted Inlet Ionisation ("SAII") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer further comprises a device arranged and adapted to supply an AC or RF voltage to the electrodes. The AC or RF voltage preferably has an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage preferably has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The mass spectrometer may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

BRIEF DESCRIPTION OF THE DRAWINGS

Various embodiments of the present invention together with other arrangements given for illustrative purposes only will now be described, by way of example only, and with reference to the accompanying drawings in which:

FIG. 14 shows an example potential diagram for a grounded time of flight tube operated in a positive ion mode;

FIG. 15 shows an example potential diagram for a grounded time of flight tube operated in a negative ion mode.

DETAILED DESCRIPTION OF PREFERRED EMBODIMENT

A preferred embodiment of the present invention will now be described.

Time of Flight ("TOF") mass spectrometers are analytical devices which are capable of detecting a complete mass spectrum of ions over a wide mass range typically every 10's of microseconds. Time of Flight mass spectrometers need to have a fast digitisation rate which in state of the art instruments may be of the order of a few hundred picoseconds.

Optical streak cameras are typically required to take a fast snapshot of time (frame) with very high time resolution but the frames are normally considerably separated in time. For a Time of Flight mass spectrometer, however, it is essential to have a continuous frame rate so that all events arriving in all time windows are registered.

The frame rate of a streak camera is analogous to the bin rate of a conventional Time of Flight digitiser (which may comprise either an Analogue to Digital Converter or a Time to Digital Converter).

Figure 1:
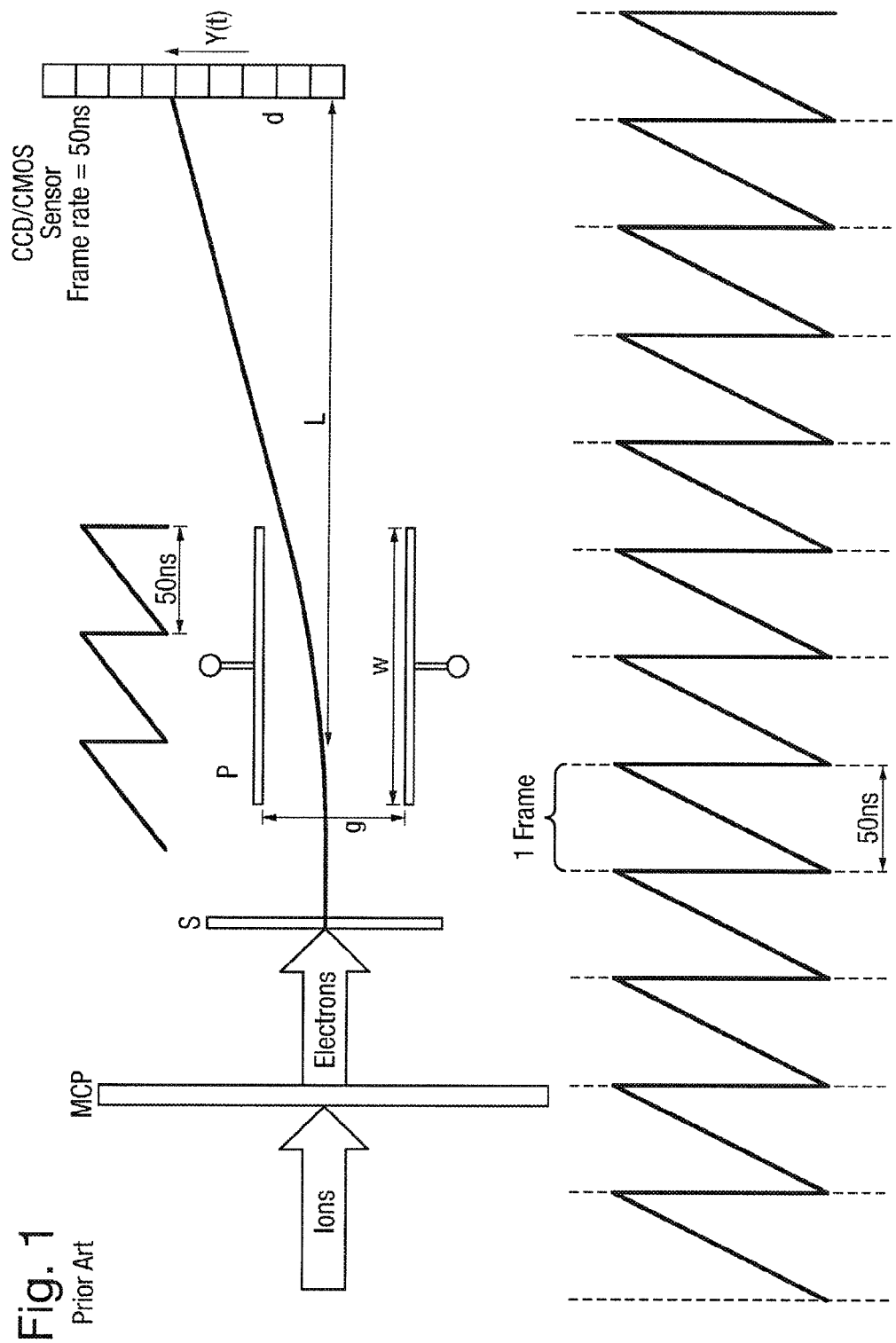
FIG. 1 illustrates a known streak camera ion detector.

The principle of operation of a streak camera is shown in FIG. 1. Ions are input upon a microchannel plate detector which emits a beam of electrons which are arranged to pass between two deflection electrodes. A sawtooth voltage is applied to the deflection electrodes and the electrons are deflected onto a CCD/CMOS sensor having a frame rate of 50 ns.

However, deflecting electrons at high frame digitisation frequencies which are compatible with current state of the art Time of Flight mass spectrometers (i.e. typically 10 GHz) would require complex, technically very challenging and expensive power supplies which would render them uncommercial.

Furthermore, the problem is compounded by the desire for a linear ramp which from Fourier analysis has higher frequency components than the fundamental digitisation rate.

In contrast to a conventional linear ramp, a sinusoidal deflection scheme may be considered. It is then possible to employ resonant circuitry to generate the deflection voltages which greatly simplifies the circuitry. Resonant circuits are often characterised by a "Q" factor which is defined as follows:

$$Q = \text{frequency} \times \text{average energy stored}/(\text{energy loss/second}) \quad (1)$$

Moderately high Q factors of several hundred are possible using lumped components at lower frequencies.

At higher microwave frequencies Q factors of ten thousand are achievable using cylindrical or rectangular cavities known as resonators which support standing waves inside them. This technology is commonly used in linear accelerators where a charged particle surfs on the crest of a travelling wave accelerating to relativistic velocities.

According to a preferred embodiment of the present invention a modified streak camera is utilised to deflect electrons in synchronisation with a digitiser which is preferably running with a bin width of e.g. 100 ps.

Figure 2:
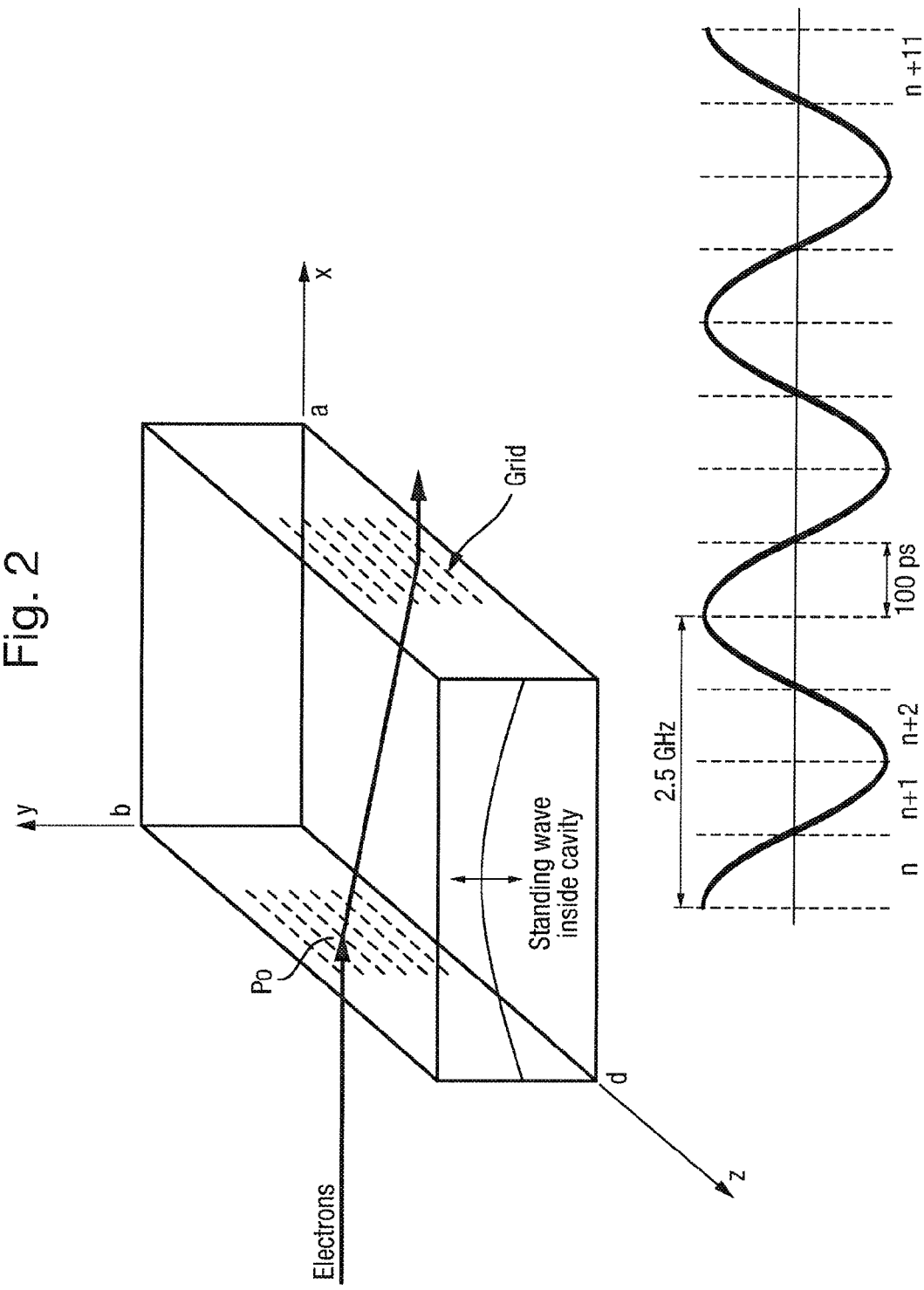
FIG. 2 shows the basic principle of operation of a microwave cavity resonator as utilised according to a preferred embodiment of the present invention in order to deflect a beam of electrons.

FIG. 2 shows the basic principle of operation of a microwave cavity resonator according to a preferred embodiment of the present invention.

According to a preferred embodiment a TE101 (transverse electric) mode electromagnetic standing wave is preferably generated or otherwise established within a microwave cavity resonator. The TE101 standing wave is preferably arranged to cause sinusoidal modulation of electrons in the y-direction of the coordinate system shown in FIG. 2.

Figure 3:
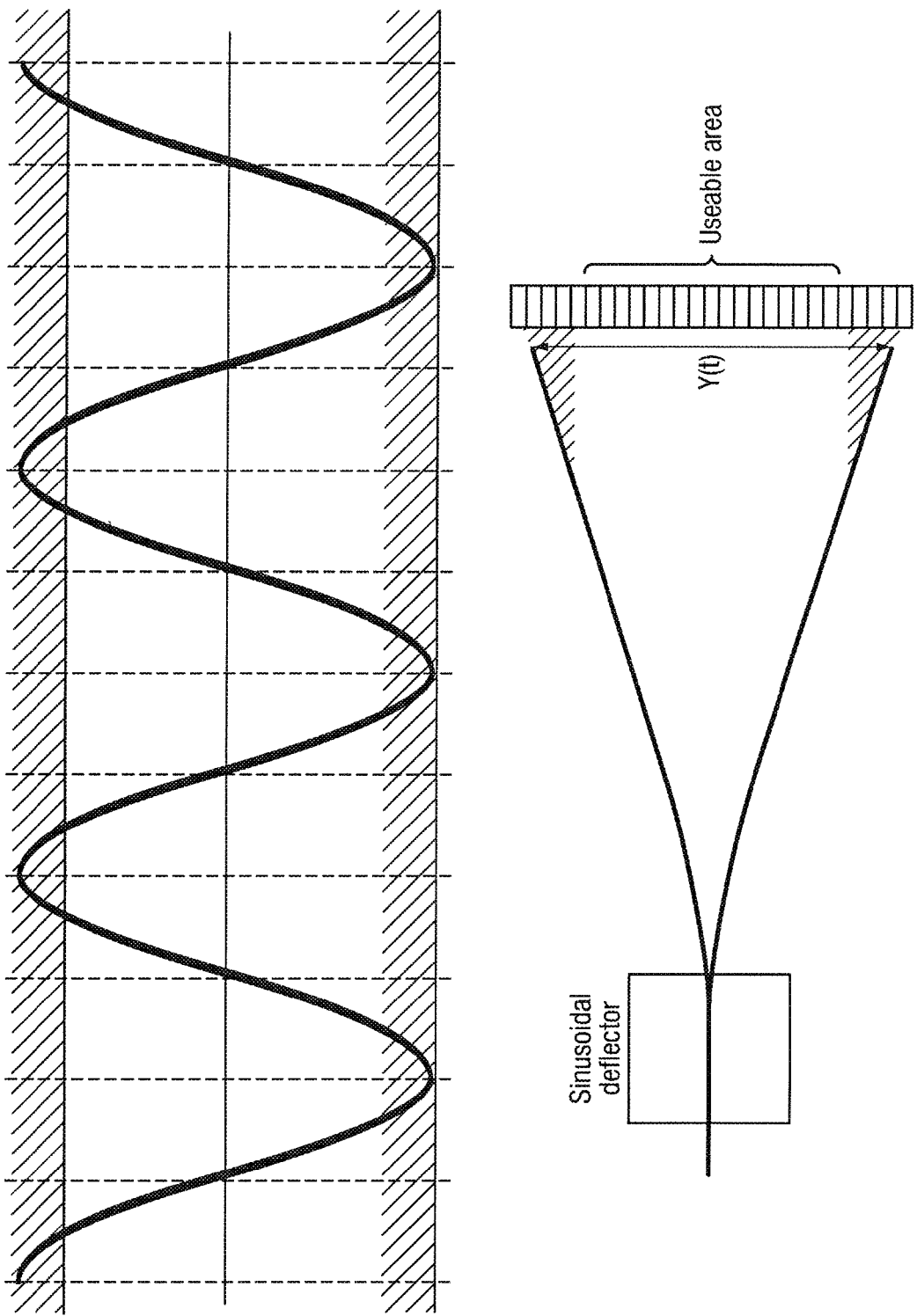
FIG. 3 illustrates the difficulty of interpolating the time that a beam of electrons modulated by a sine wave impacts a position sensitive detector towards the top and bottom of the sine wave.

As will be understood with reference to FIG. 3, the nonlinear vertical deflection characteristic makes it more difficult to interpolate the time towards the top and bottom of the sine wave as shown in FIG. 3. However, if the start signal is truly asynchronous with the detection system clock, then ions which are difficult to interpolate may simply be rejected without introducing any bias into the acquired mass spectrum.

In an asynchronous system rejecting some of the ions merely reduces the overall transmission of the spectrometer as the probability of any individual ion arriving in any particular time is uniform.

Figure 4:
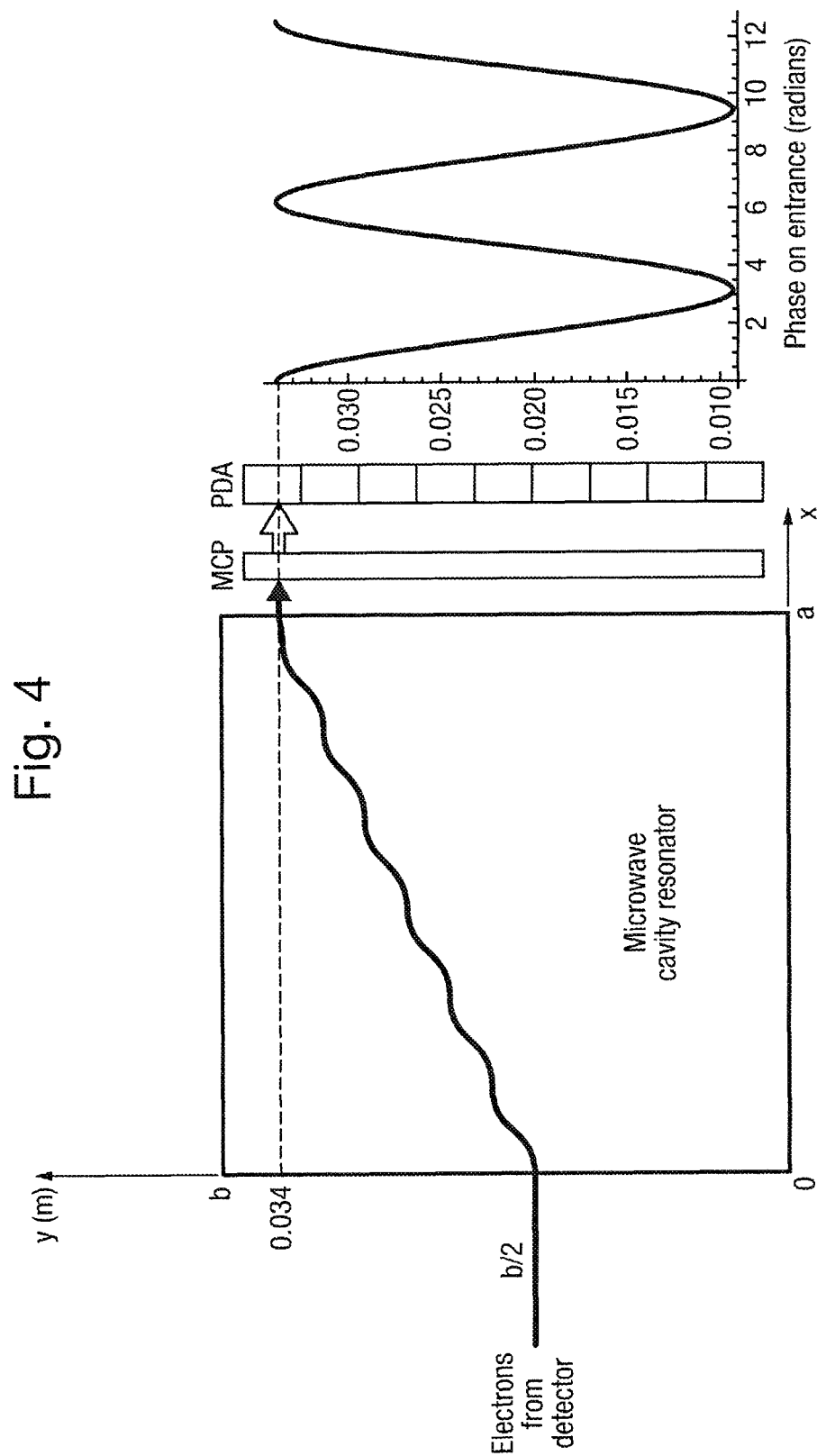
FIG. 4 shows a typical trajectory of an electron being deflected by a TE101 mode established within a microwave cavity resonator according to a preferred embodiment of the present invention.

FIG. 4 shows a typical trajectory of an electron being deflected by a TE101 mode established within a microwave cavity resonator according to an embodiment of the present invention. Electrons preferably arrive in the middle of the guide or microwave cavity resonator at a displacement y=b/2 and are preferably accelerated by the electromagnetic field. With this mode and input conditions the electron motion is largely dominated by the electric component of the electromagnetic field in the y-direction and the output coordinate is a function of the initial phase of electromagnetic wave that the electron sees on entry into the device.

Figure 5:
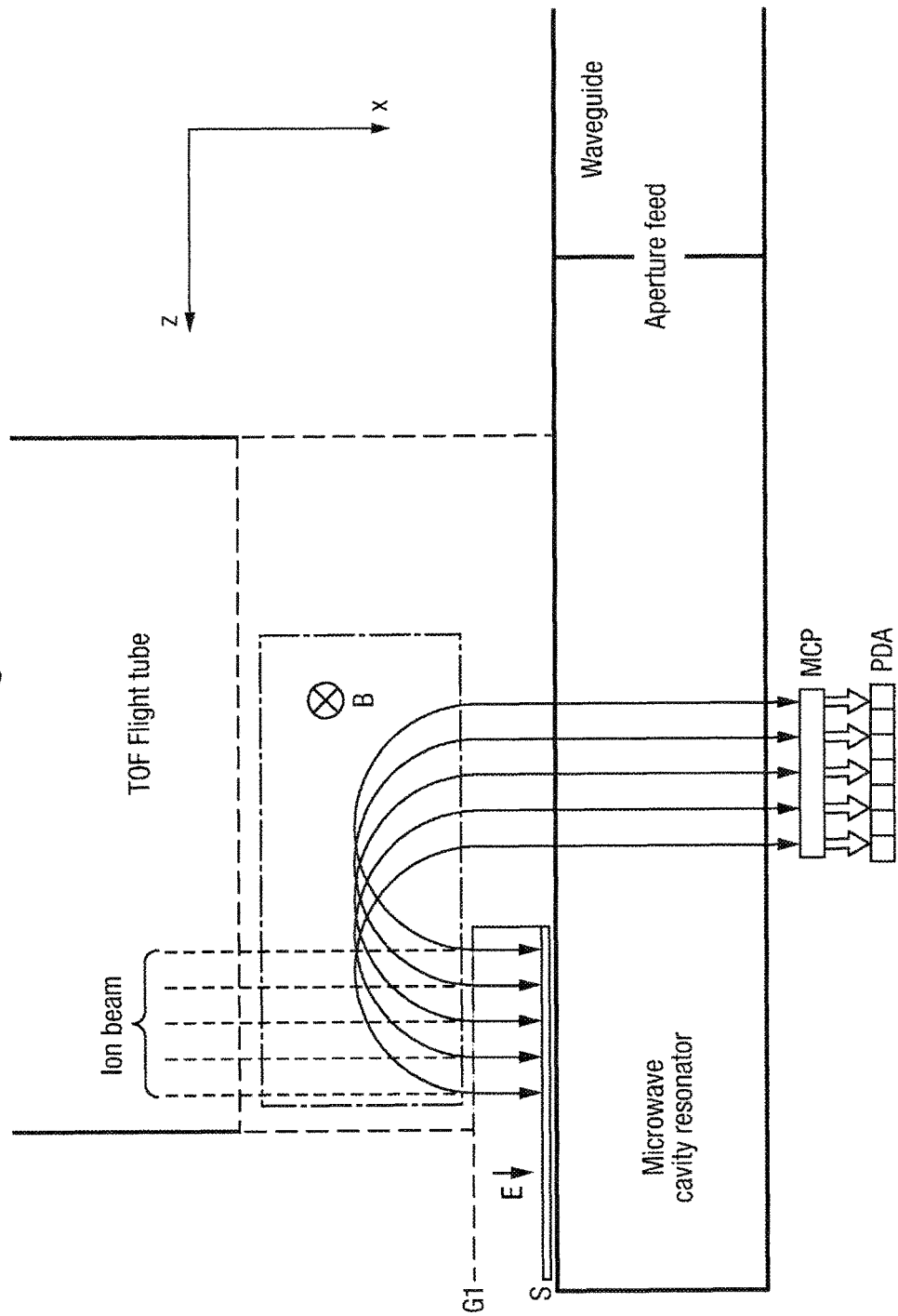
FIG. 5 shows a preferred embodiment of the present invention wherein an incoming beam of ions is caused to strike a conversion dynode whereupon secondary electrons are liberated therefrom and are directed by a magnetic field through a microwave cavity resonator towards a microchannel plate detector and associated position sensitive detector.

FIG. 5 shows a preferred embodiment of the present invention wherein incoming ions are arranged to strike a conversion dynode S whereupon secondary electrons are liberated therefrom. The embodiment shown in FIG. 5 is in contrast to the known arrangement wherein output electrons from a microchannel plate are deflected by the sweep voltage.

This is an important distinction because the output electron shower from a microchannel plate in the known arrangement is typically of the order of several hundred picoseconds which is longer than the digitisation period which according to the preferred embodiment may only be 100 ps. As a result, it is apparent that sub bin interpolation at the 10 ps level or so is impossible using the known arrangement.

The secondary electrons emitted from the conversion dynode S according to the preferred embodiment of the present invention are advantageously created almost instantaneously by the conversion dynode S. The creation of the secondary electrons does not contribute to temporal broadening of the signal. This represents a significant advantage over the known arrangement which uses a microchannel plate detector.

The secondary electrons according to the preferred embodiment are preferably accelerated from the conversion surface S by a relative potential of e.g. 1000V held on a grid electrode G1 so that the secondary electrons pass the grid electrode G1. The secondary electrons are then preferably bent round past the grid electrode G1 and the conversion surface S by a magnetic field B which is preferably applied in a direction perpendicular to the trajectory of the electrons.

The secondary electrons are then preferably directed into a microwave cavity resonator which preferably has a hole, grid or input port through which the electrons preferably pass in order to enter into the microwave cavity resonator. The magnetic and electric fields of the conversion and acceleration stages of the detector are preferably arranged so that the electrons adopt isochronous trajectories which are preferably independent of the initial strike position of ions on the conversion dynode S.

The ions preferably arrive at the microwave cavity resonator in a narrow stripe in the z-direction with only a small extent in the y-dimension so that a subsequent y-deflection within the microwave cavity resonator is substantially only a function of the initial z-coordinate and phase.

Ions which are incident upon the conversion dynode S have preferably been accelerated through a time of flight region of an orthogonal Time of Flight mass analyser. The ions are preferably initially orthogonally accelerated into the time of flight region by applying a large voltage pulse (several kV) to one or more orthogonal acceleration electrodes. The voltage pulse typically has a rise time of the order of 10's of nanoseconds.

Time of Flight line widths at the nanosecond level are still possible because the ion flight times depend on the integral of the accelerating field rather than its rise time. Nevertheless, measurement of the initiation of the acceleration pulse known as the start signal must be made very precisely otherwise resolution will deteriorate over signals that are the integration of many discrete pushes.

In order to realise the full benefit of modified streak camera detection of ions at the sub bin level according to the preferred embodiment of the present invention it is advantageous to measure the acceleration pulse with the same precision as the detected ions.

Figure 6:
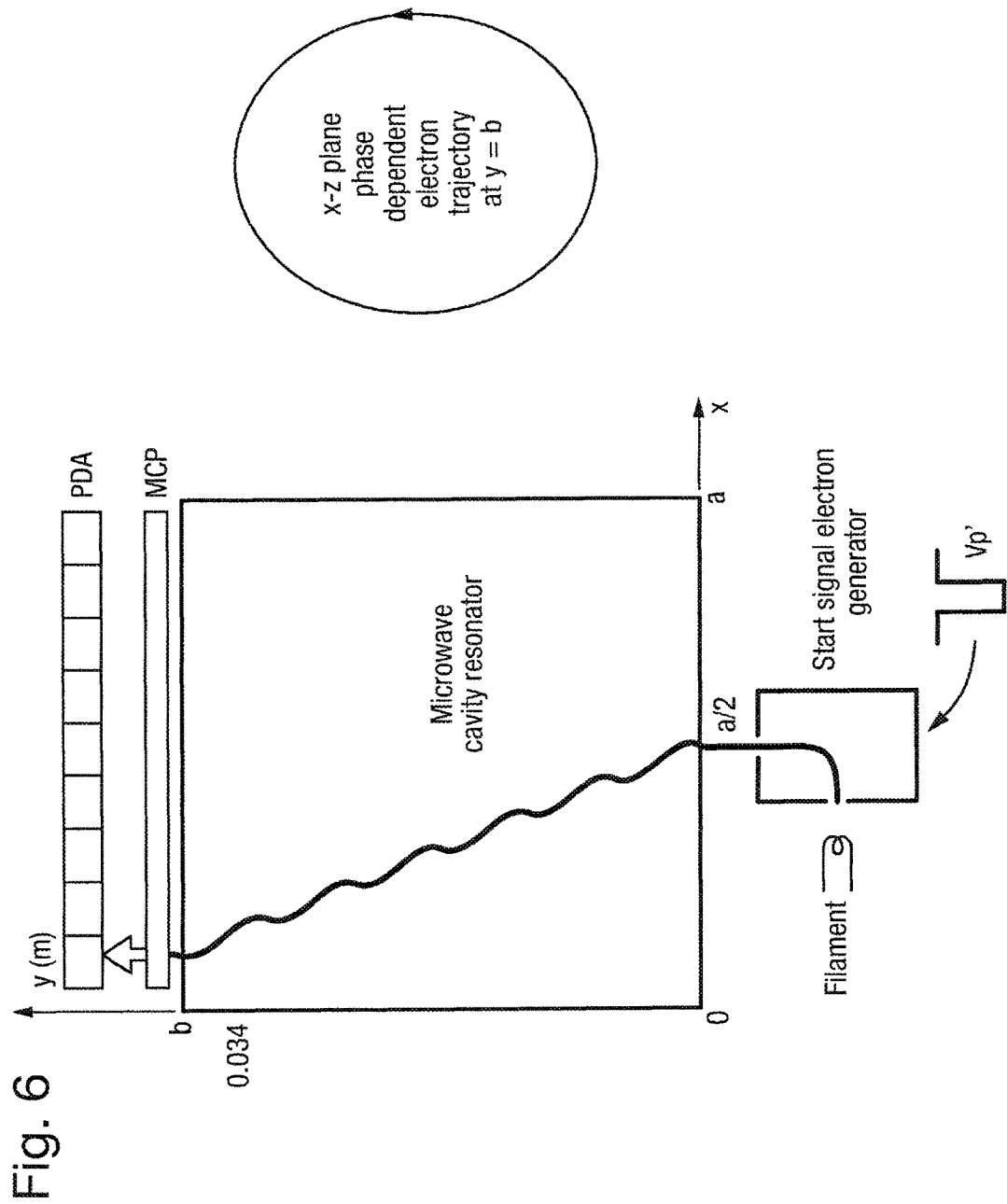
FIG. 6 shows how according to an embodiment of the present invention a separate beam of electrons generated by a filament may be used to measure the rising edge of the main acceleration voltage pulse.

In order to increase the precision of start timing a separate small pulsed electron beam is preferably utilised according to an embodiment of the present invention. The start electron beam is preferably measured using the same modified streak camera principle in a manner as shown in FIG. 6.

The pulse for ejecting the start electron beam using a filament is preferably derived from or is otherwise dependent upon the main acceleration pulse using passive components. As a result there is advantageously no inherent jitter with the main pulse.

According to a preferred embodiment the start electron device preferably produces a pulse of electrons using a filament which is preferably a measure of the rising edge of the main acceleration voltage pulse of the mass spectrometer. The start signal electrons are preferably passed through the guide or microwave cavity resonator in a different direction to those secondary electrons emitted from the detection surface of the conversion dynode. The step of passing the start electrons through the TE101 mode established within the microwave cavity resonator in the y-direction with certain initial conditions results in the start electrons undertaking an elliptical trajectory. Each pixel of the photodiode array then represents a different interpolated time leading to start time precision better than 10 ps.

Figure 7:
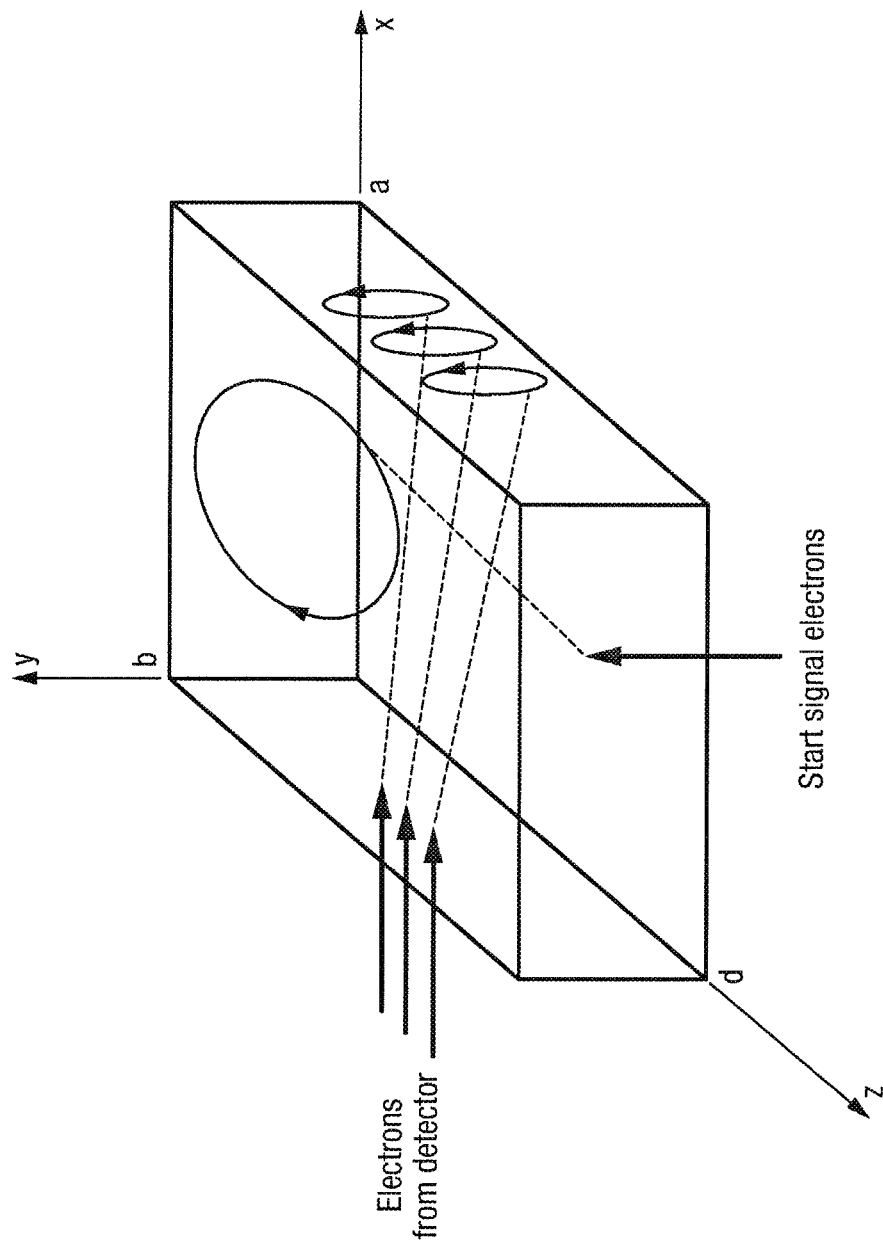
FIG. 7 shows the different trajectories followed both by start electrons and also by secondary electrons emitted from the conversion dynode in a single guide.

FIG. 7 shows the different trajectories followed both by start electrons and by secondary electrons emitted from the detection surface of the conversion dynode in a single guide or microwave cavity resonator.

Figure 8:
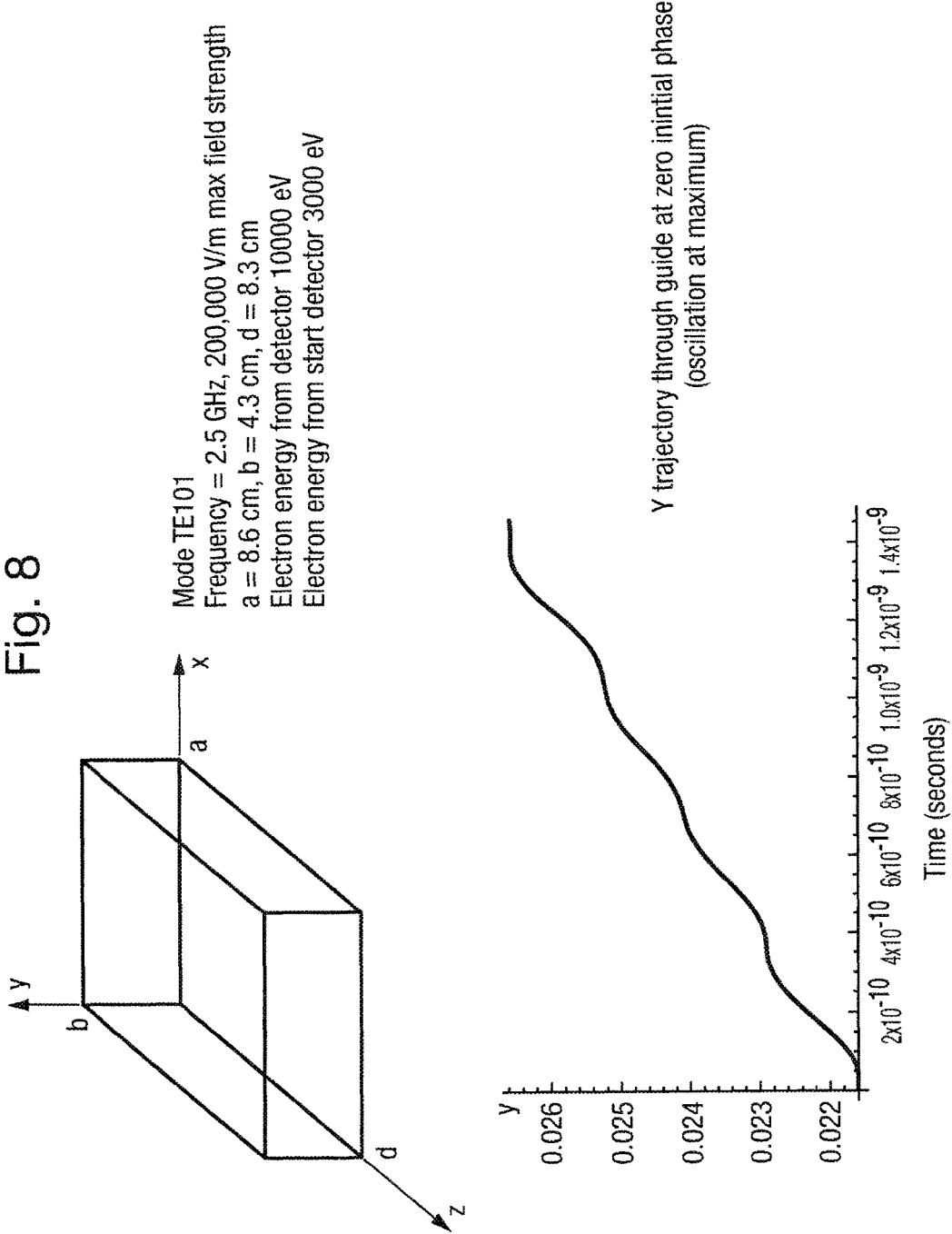
FIG. 8 illustrates a preferred geometry for a rectangular cavity resonator at 2.5 GHz for the TE101 mode and a typical electron trajectory.

FIG. 8 illustrates the geometry for a rectangular cavity resonator at 2.5 GHz for a TE101 mode and also a typical electron trajectory.

Figure 9:
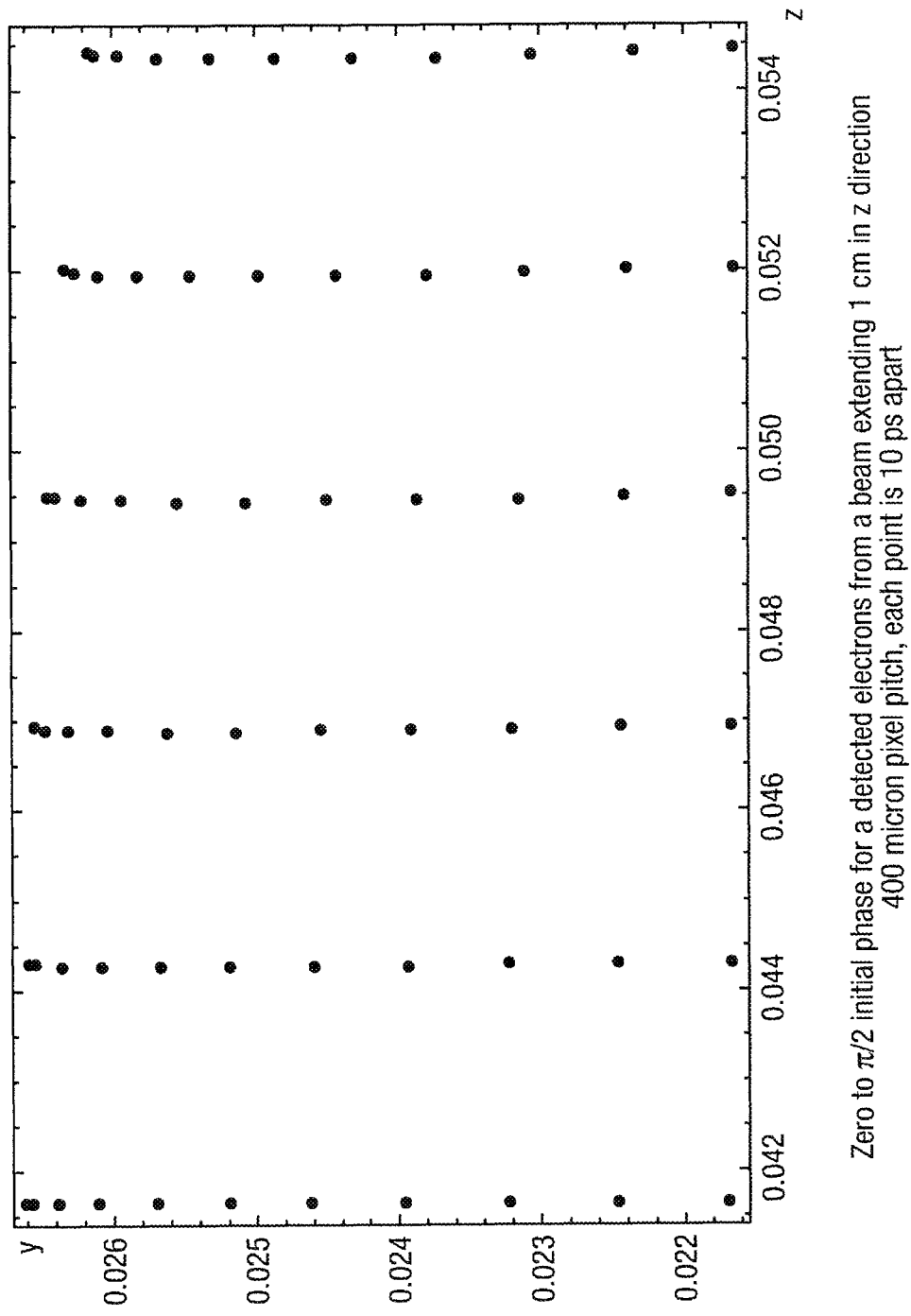
FIG. 9 illustrates how an electron beam extending 1 cm in the z-direction is deflected across a pixelated detector having a 400 µm pitch according to an embodiment of the present invention.

FIG. 9 illustrates how a beam extending 1 cm in the z-direction is deflected across a pixelated detector having a 400 µm pitch.

Figure 10:
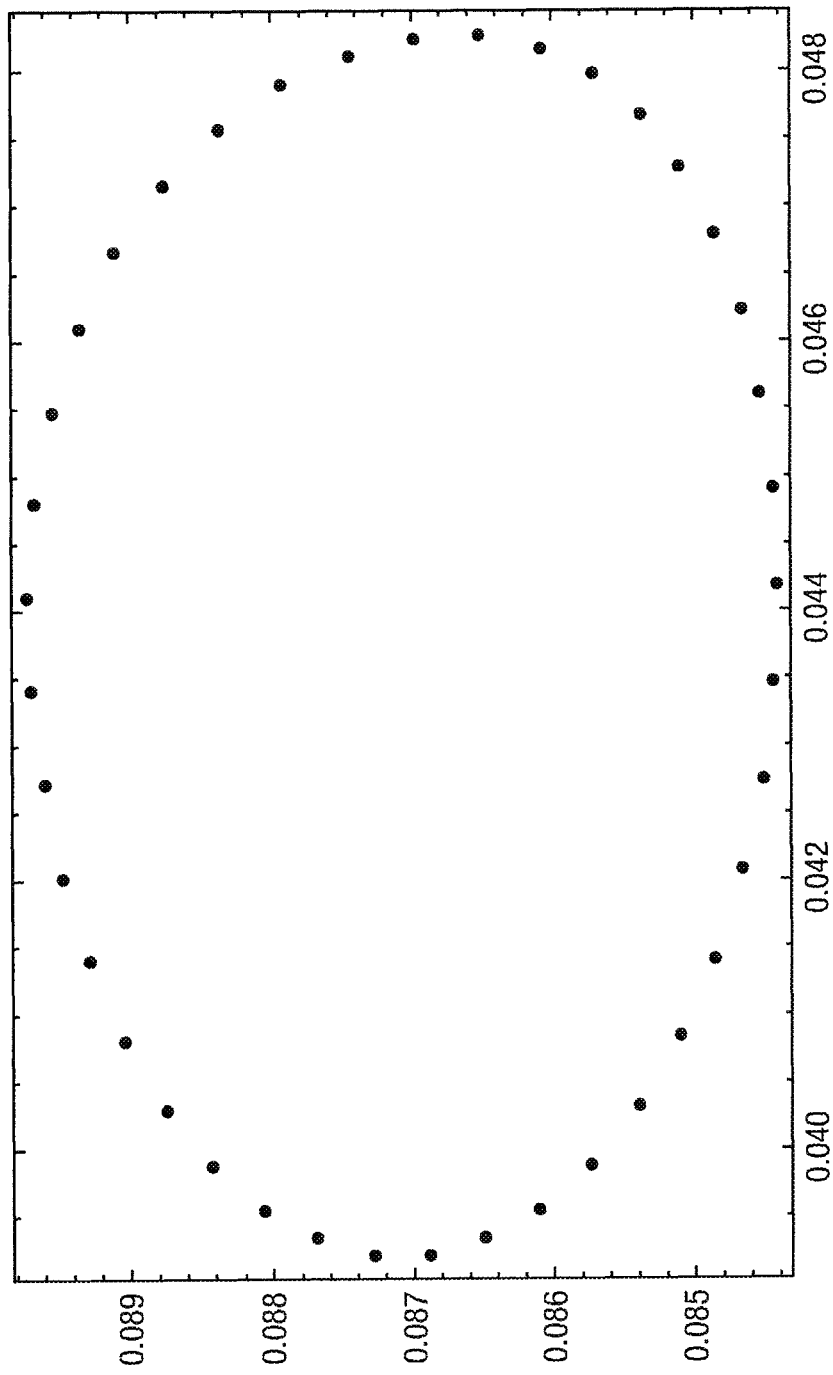
FIG. 10 illustrates how the signal from a pulsed start electron beam describes an elliptical trajectory.

FIG. 10 shows how the signal from the start electron beam describes an elliptical trajectory.

It will be noted that FIG. 9 shows evidence of a small y-deflection that has a dependence in the z-direction. This is to be expected as the maximum deflection is produced at the peak of the standing wave which is centred at d/2 (z=41.5 mm). This dependence may be accounted for by appropriate calibration of the device.

Figure 11:
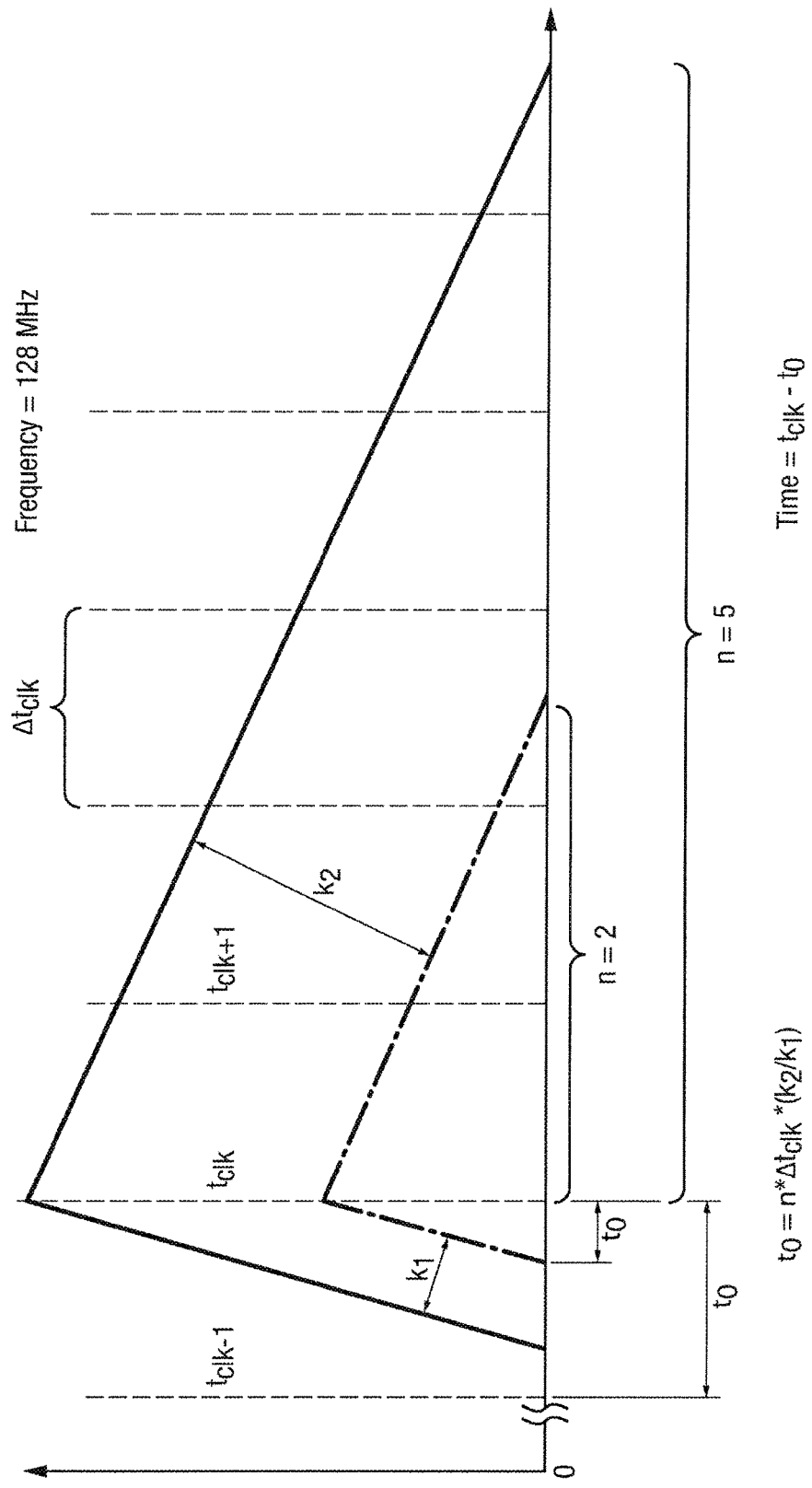
FIG. 11 illustrates a dual edge TDC principle.

According to a preferred embodiment of the present invention it is advantageous to use the oscillating frequency of the microwave cavity resonator to act as the master clock for the spectrometer system. An example of a 100 ps bin width digitiser circuit is a Wilkinson converter. The principle of operation is one of so called time stretching wherein the clock runs at a relatively low rate of 100 MHz (bin width 10 ns). A voltage ramp of a certain time constant is created at the beginning of each clock cycle. The arrival of an event causes the ramp to be stopped and ramped down at a different lower rate typically determined by the ratio of two capacitors. This principle is shown in FIG. 11.

A time stretching ratio of 100 allows 100 ps bin widths to be created from a 100 MHz clock. It will be apparent that the highest frequency existing in the Time of Flight mass spectrometer is the 2.5 GHz of the microwave cavity resonator which can be divided down to serve all other clock frequencies in the instrument thereby ensuring phase locking of all frequencies.

The various embodiments described above relate to analysis of positively charged ions. However, other embodiments are also contemplated wherein negatively charged ions may be analysed.

FIGS. 12-15 illustrate how the ion detector system according to the present invention may be arranged to analyse either positively charged ions or negatively charged ions. In particular, FIGS. 12-15 show potential diagrams for both a positive ion mode of operation and a negative ion mode of operation.

Figure 12:
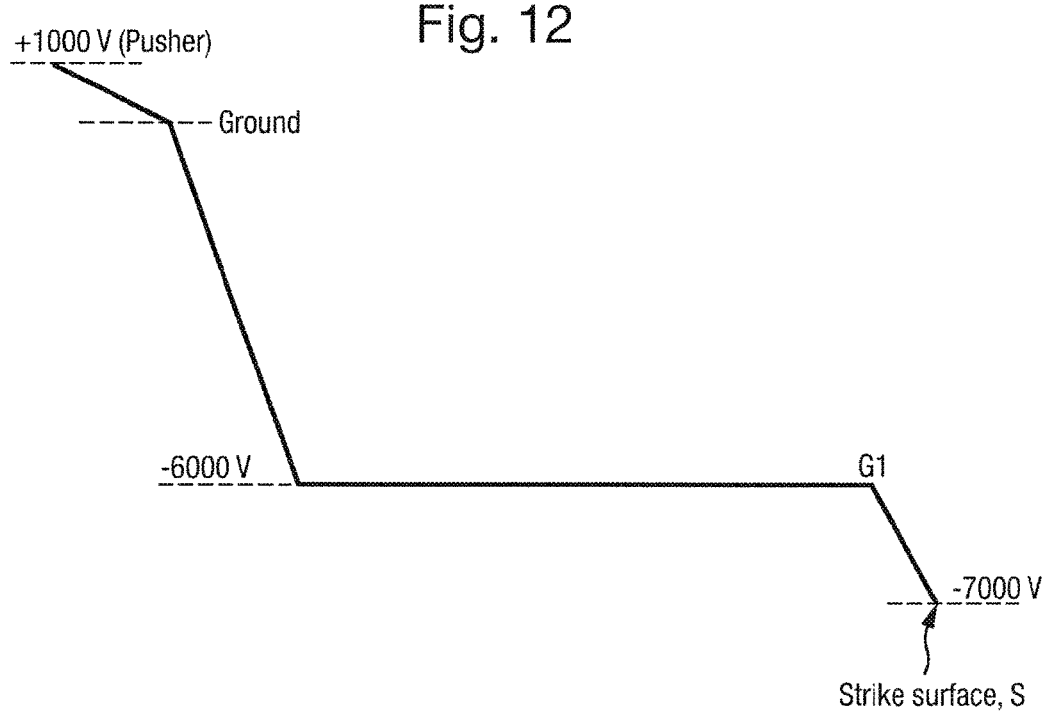
FIG. 12 shows an example potential diagram for a floated time of flight tube operated in a positive ion mode.

FIG. 12 shows a potential diagram according to an embodiment of the present invention when the time of flight tube is floated and is operated in a positive ion mode. As shown, the pusher electrode is maintained at a potential of e.g. 1000 V and a grid electrode is maintained at ground or 0 V i.e. the applied pusher voltage ΔV is 1000 V. The entrance and exit of the time of flight tube is maintained at −6000 V as is the grid electrode G1 which is arranged adjacent the conversion dynode or strike surface S. The conversion dynode or strike surface S is preferably maintained at a potential of −7000 V.

Figure 13:
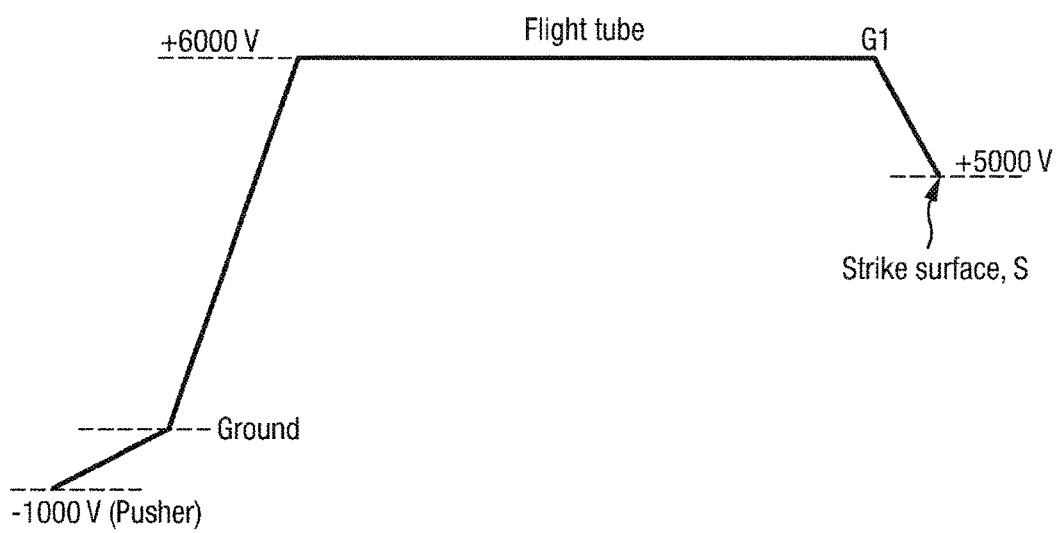
FIG. 13 shows an example potential diagram for a floated time of flight tube operated in a negative ion mode.

FIG. 13 shows a potential diagram according to an embodiment of the present invention when the time of flight tube is floated and is operated in a negative ion mode. The pusher electrode is maintained at −1000 V and a grid electrode is maintained at ground or 0 V i.e. the applied pusher voltage $\Delta V$ is −1000 V. The entrance and exit of the time of flight tube is maintained at 6000 V as is the grid electrode G1 which is arranged adjacent the conversion dynode or strike surface S. The conversion dynode or strike surface S is preferably maintained at a potential of 5000 V.

FIG. 14 shows a potential diagram according to an embodiment of the present invention when the time of flight tube is grounded and is operated in a positive ion mode. As shown, the pusher electrode is maintained at a potential of e.g. 7000 V and a grid electrode is maintained at 6000 V i.e. the applied pusher voltage $\Delta V$ is 1000 V. The entrance and exit of the time of flight tube is maintained at ground or 0V as is the grid electrode G1 which is arranged adjacent the conversion dynode or strike surface S. The conversion dynode or strike surface S is preferably maintained at a potential of −1000 V.

FIG. 15 shows a potential diagram according to an embodiment of the present invention when the time of flight tube is grounded and is operated in a negative ion mode. As shown, the pusher electrode is maintained at a potential of e.g. −7000 V and a grid electrode is maintained at −6000 V i.e. the applied pusher voltage $\Delta V$ is −1000 V. The entrance and exit of the time of flight tube is maintained at ground or 0V as is the grid electrode G1 which is arranged adjacent the conversion dynode or strike surface S. The conversion dynode or strike surface S is preferably maintained at a potential of −1000 V.

As is apparent from FIGS. 12-15 the potential of the grid electrode G1 is preferably always higher than the potential of the conversion dynode or strike surface S irrespective of whether or not the time of flight tube is floated or grounded and irrespective of whether or not the ion detector system is operated in a positive ion mode or a negative ion mode. Accordingly, electrons emitted from the conversion dynode or strike surface S will be accelerated towards the grid electrode G1.

Figure 16:
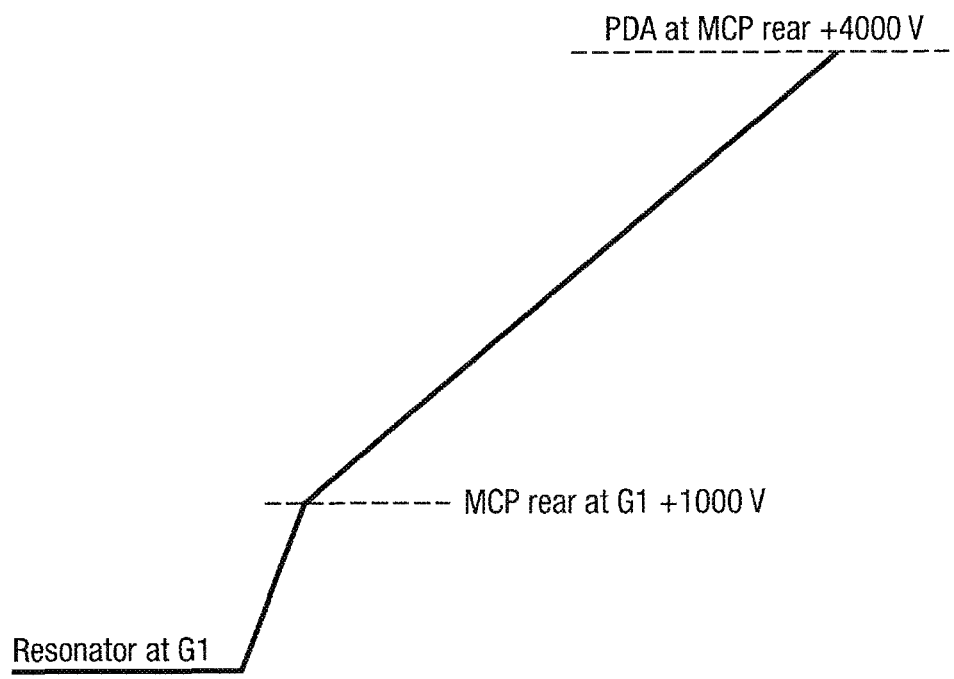
FIG. 16 shows an example potential diagram for a microwave cavity resonator, associated microchannel plate detector and photodiode array according to an embodiment of the present invention.

FIG. 16 shows an example potential diagram illustrating the relative potential differences which are preferably maintained between the microwave cavity resonator, the microchannel plate (MCP) which is preferably provided at the exit of the microwave cavity resonator and the position sensitive detector which preferably comprises a photodiode array (PDA) which is preferably arranged to receive electrons emitted from the rear of the microchannel plate.

The microwave cavity resonator is preferably held at the same potential as the grid electrode G1. The initial strike surface of the microchannel plate may be held at the same potential as the grid electrode G1. A potential difference of +1000 V is preferably maintained across the microchannel plate so that the rear (output) end of the microchannel plate is preferably held at a potential +1000 V higher than that of the front (input) end of the microchannel plate.

According to a preferred embodiment the position sensitive detector which preferably comprises a photodiode array is preferably held at a potential 4000 V higher than the potential at the rear (output) end of the microchannel plate. However, it should be apparent to those skilled in the art that other suitable potential differences may be used.

In the embodiments described above, an acceleration of the electrons liberated at the conversion dynode S to 1000 V by passing the electrons back through the grid electrode G1 is preferably sufficient to give enough gain in the microchannel plate MCP without having any substantial adverse effect on the ion conversion efficiency at the conversion dynode S.

Alternative embodiments are contemplated wherein alternative modes to a TE101 mode may be employed. For example, according to other embodiments a transverse magnetic ("TM") mode or higher order transverse electric modes may be utilised with the microwave cavity resonator.

The modified streak camera utilising a microwave cavity resonator may be utilised in other applications other than Time of Flight mass spectrometers.

Other embodiments are contemplated wherein a small pulsed electron start signal may be utilised to reduce jitter of a Time of Flight detector system which does not necessarily utilise a modified streak camera detector system.

Although the present invention has been described with reference to preferred embodiments, it will be understood by those skilled in the art that various changes in form and detail may be made without departing from the scope of the invention as set forth in the accompanying claims.

The invention claimed is:

1. An ion detector system for a mass spectrometer comprising:
a first device arranged and adapted to receive ions and emit or output first electrons; and
a microwave resonator arranged and adapted to deflect said first electrons onto a first detector.

2. An ion detector system as claimed in claim 1, wherein said first device comprises a conversion dynode.

3. An ion detector system as claimed in claim 1, wherein said first electrons comprise secondary electrons.

4. An ion detector system as claimed in claim 1, further comprising one or more grid electrodes arranged upstream of said first device wherein said one or more grid electrodes are arranged and adapted to accelerate said ions onto or into said first device.

5. An ion detector system as claimed in claim 1, further comprising a second device arranged and adapted to apply a magnetic field so as to deflect said first electrons towards said microwave resonator.

6. An ion detector system as claimed in claim 1, wherein said first detector comprises one or more microchannel plates.

7. An ion detector system as claimed in claim 1, wherein said first detector is arranged downstream of said microwave resonator.

8. An ion detector system as claimed in claim 1, wherein said first detector is arranged and adapted to receive said first electrons and emit or output second electrons.

9. An ion detector system as claimed in claim 8, further comprising a first position sensitive detector ("PSD") arranged and adapted to detect the position or location that said second electrons impinge upon said first position sensitive detector.

10. An ion detector system as claimed in claim 1, wherein said microwave resonator is arranged and adapted to generate electromagnetic waves within said microwave resonator.

11. An ion detector system as claimed in claim 10, wherein said microwave resonator is arranged and adapted to cause said electromagnetic waves to form standing waves within said microwave resonator.

12. An ion detector system as claimed in claim 11, wherein in a mode of operation said standing waves are arranged so as to sinusoidally modulate said first electrons as said first electrons pass through said microwave resonator.

13. A mass spectrometer comprising:
an ion detector system as claimed in claim 1; and
a Time of Flight mass analyser; wherein said Time of Flight mass analyser comprises:
a time of flight region; and
one or more orthogonal acceleration electrodes for orthogonally accelerating ions into said time of flight region; and
wherein the mass spectrometer further comprises a device arranged and adapted to apply a voltage pulse to said one or more orthogonal acceleration electrodes in order to cause ions to be orthogonally accelerated into said time of flight region.

14. A mass spectrometer as claimed in claim 13, further comprising a device arranged and adapted to generate a beam of third electrons at substantially the same time that said voltage pulse is applied to said one or more orthogonal acceleration electrodes or that ions are orthogonally accelerated into said time of flight region.

15. A mass spectrometer as claimed in claim 14, wherein said third electrons are passed, in use, through said microwave resonator.

16. A mass spectrometer as claimed in claim 15, wherein:
said third electrons are passed, in use, through said microwave resonator in a different direction to the direction of transmission of said first electrons through said microwave resonator; and
the mass spectrometer further comprises:
a third detector arranged and adapted to receive said third electrons and emit or output fourth electrons;
a second position sensitive detector ("PSD") arranged and adapted to detect the position or location that said fourth electrons impinge upon said second position sensitive detector; and
a control system arranged and adapted to determine from the detected position or location that said fourth electrons impinge upon said second position sensitive detector a measure of the rising edge of said voltage pulse applied to said one or more orthogonal acceleration electrodes.

17. A mass spectrometer as claimed in claim 13, further comprising a master clock wherein clock cycles of said master clock are derived from a signal applied to said microwave resonator.

18. A method of detecting ions comprising:
receiving ions on a first device and emitting or outputting first electrons; and
deflecting said first electrons onto a first detector using a microwave resonator.

19. A photon detection system comprising:
a first device arranged and adapted to receive photons to be detected and to emit or output first electrons as a result of receiving said photons to be detected; and
a microwave resonator arranged and adapted to deflect said first electrons onto a first detector.

20. A method of detecting photons comprising:
receiving photons to be detected on a first device and said first device emitting or outputting first electrons as a result of receiving said photons to be detected; and
deflecting said first electrons onto a first detector using a microwave resonator.

* * * * *